United States Patent [19]

VandenBerg

[11] Patent Number: Plant 6,880

[45] Date of Patent: Jun. 27, 1989

[54] CHRYSANTHEMUM PLANT NAMED YELLOW KARDO

[75] Inventor: Cornelis P. VandenBerg, Salinas, Calif.

[73] Assignee: Yoder Brothers, Inc., Barberton, Ohio

[21] Appl. No.: 173,081

[22] Filed: Mar. 25, 1988

[51] Int. Cl.[4] ..... A01H 5/00

[52] U.S. Cl. ..... Plt./74

[58] Field of Search ..... Plt./74

*Primary Examiner*—Robert E. Bagwill

*Attorney, Agent, or Firm*—Foley & Lardner, Schwartz, Jeffery, Schwaab, Mack, Blumenthal & Evans

[57] ABSTRACT

A Chrysanthemum plant named Yellow Kardo particularly characterized by its flat capitulum form; daisy capitulum type; yellow ray floret color; diameter across face of capitulum of up to 11 cm at maturity; uniform nine week photoperiodic flowering response to short days; peduncle length ranging from 15 to 23 cm; tall plant height when grown as a single stem cut mum; and excellent tolerance to low temperatures for bud initiation and flower development.

3 Drawing Sheets

The present invention comprises a new and distinct cultivar of Chrysanthemum, botanically known as *Dendranthema grandiflora,* and referred to by the cultivar name Yellow Kardo.

Yellow Kardo, identified as 79L40A01, is a product of a mutation induction program which had the objective of creating new Chrysanthemum cultivars that would expand the color range of an existing cultivar while retaining all other traits.

Yellow Kardo was discovered and selected by a technician working under formulations established by Cornelis P. VandenBerg in February of 1986 in a controlled environment in Alva, Fla. as one flowering plant within a flowering block established as rooted cuttings from stock plants which had been exposed as unrooted cuttings to an X-ray source of 200 rads. The irradiated parent was the cultivar identified as Kardo, disclosed in U.S. Plant Pat. No. 6,050.

The first act of asexual reproduction of Yellow Kardo was accomplished when vegatative cuttings were taken from the initial selection in May of 1986 in a controlled environment in Alva, Fla., by technicians working under formulations established by Cornelis P. VandenBerg.

Horticultural examination of controlled flowerings of successive plantings has shown that the unique combination of characteristics as herein disclosed for Yellow Kardo are firmly fixed and are retained through successive generations of asexual reproduction.

Yellow Kardo has not been observed under all possible environmental conditions. The phenotype may vary significantly with variations in environment such as temperature, light intensity, and daylength.

The following observations, measurements and comparisons describe plants grown in Salinas, Calif. under greenhouse conditions which approximate those generally used in commercial greenhouse practice. The low temperature tolerance was determined in repeated flowerings in Bogota, Colombia.

The following traits have been repeatedly observed and are determined to be basic characteristics of Yellow Kardo, which, in combination, distinguish this Chrysanthemum as a new and distinct cultivar:

1. Flat capitulum form.
2. Daisy capitulum type.

3. Yellow ray floret color.
4. Diameter across face of capitulum up to 11 cm at maturity.
5. Uniform nine week photoperiodic flowering response to short days.
6. Peduncle length ranging from 15 to 23 cm.
7. Tall plant height, requiring one long day week prior to short days to attain a flowered plant height of 95 to 105 cm for year-round flowerings when grown as a single stem cut mum.
8. Excellent tolerance to low temperatures for bud initiation and flower development.

The accompanying photographic drawings show typical inflorescence and leaf characteristics of Yellow Kardo, with the colors being as nearly true as possible with illustrations of this type.

Sheet 1 is a color photograph of Yellow Kardo grown as a single stem cut spray mum.

Sheet 2 is a black and white photograph of three views of the inflorescence of Yellow Kardo.

Sheet 3 is a black and white photograph showing the upper and under sides of the leaves of Yellow Kardo at three stages of development (mature, intermediate and immature).

Of the commercial cultivars known to the inventor, the most similar in comparison to Yellow Kardo is the parent cultivar Kardo. All traits of Yellow Kardo are similar to those of Kardo, except the color of ray florets and the peduncle length. Color of ray florets of Yellow Kardo is yellow. Kardo is described as having yellow-orange ray florets. The peduncle length of Yellow Kardo is less than Kardo.

In the following description, color references are made to The Royal Horticultural Society Colour Chart. The color values were determined on plant material grown in Salinas, Calif. on Oct. 12, 1987.

Classification:

*Botanical.*—*Dendranthema grandiflora,* cv Yellow Kardo.

*Commercial.*—Daisy cut spray mum.

INFLORESCENCE

A. Capitulum:

*Form.*—Flat.

*Type.*—Daisy.

*Diameter across face.*—Up to 11 cm at maturity.

B. Corolla of ray florets:

*Color (general tonality from a distance of three meters).*—Yellow.

*Color (upper surface).*—Between 7A and 9A.

*Color (under surface).*—Between 7B and 9B.

*Shape.*—Oblong, with lateral petal roll when immature.

C. Corolla of disc florets:

*Color (mature).*—Closest to 151C.

*Color (immature).*—Closest to 144A.

D. Reproductive organs:

*Androecium.*—Present on disc florets only; scant pollen.

*Gynoecium.*—Present on both ray and disc florets.

PLANT

A. General appearance:

Height.—Tall; 95 to 105 cm as a single stem cut mum with one long day week prior to short days.

B. Foliage:

*Color (upper surface).*—147A.

*Color (under surface).*—137B to 137C.

*Shape.*—Narrow, deeply lobed and sharply serrated.

I claim:

1. A new and distinct Chrysanthemum plant named Yellow Kardo, as described and illustrated, and parts thereof.

* * * * *

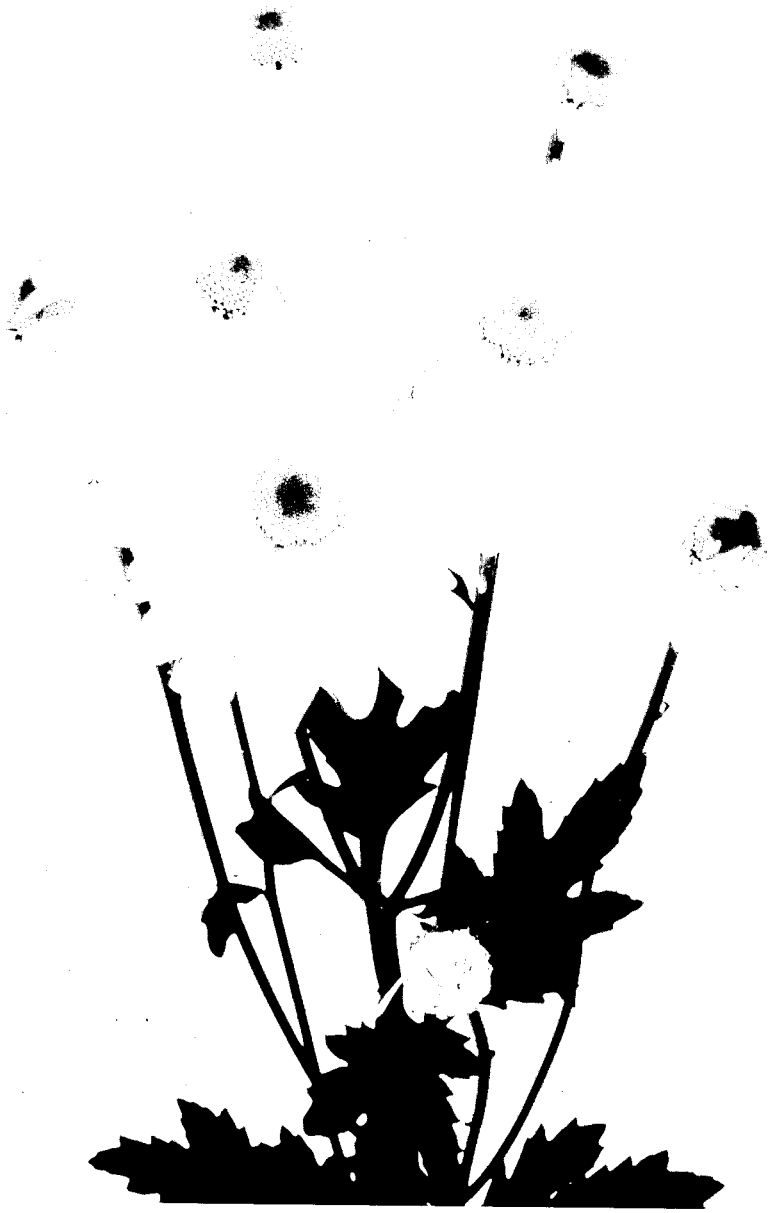

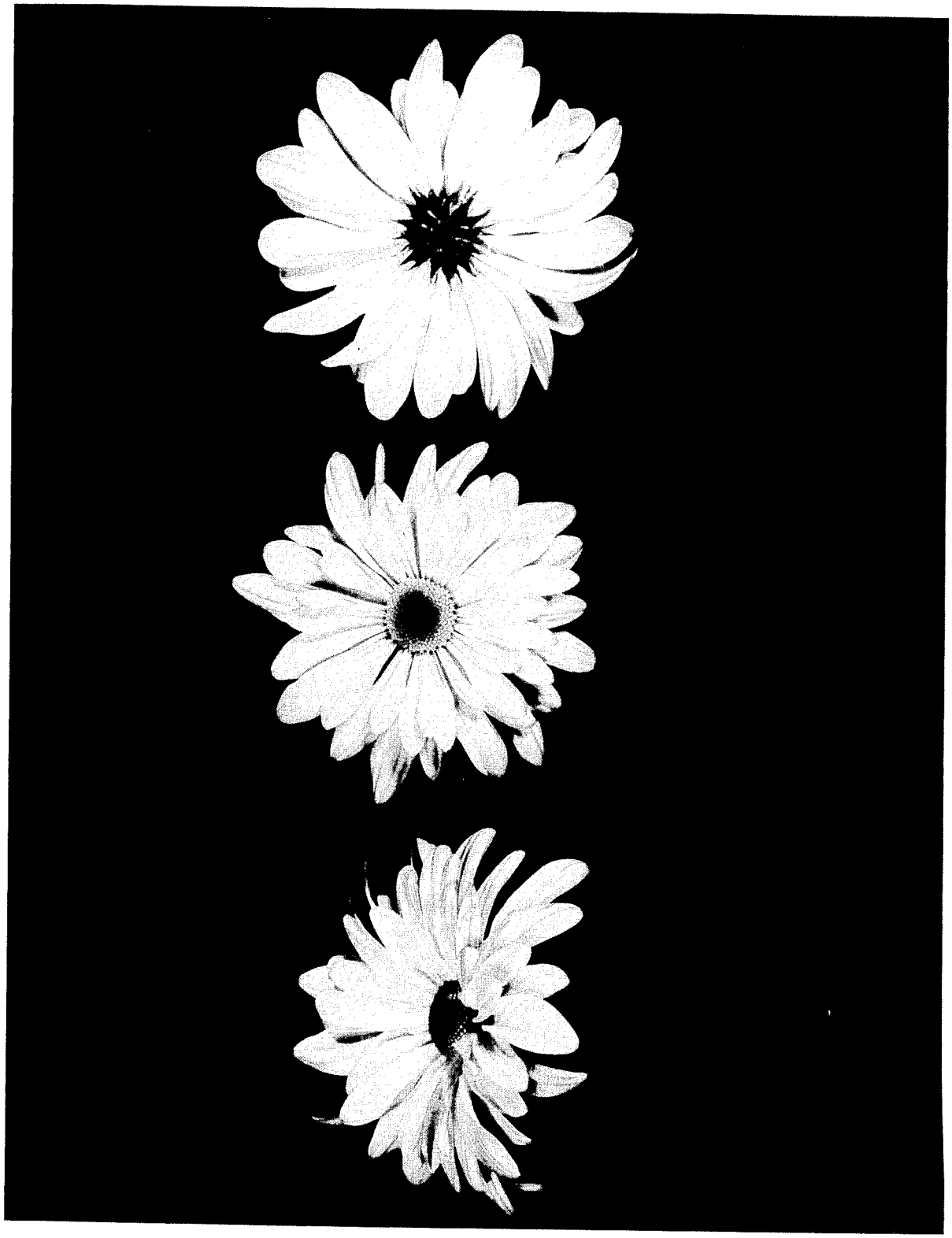

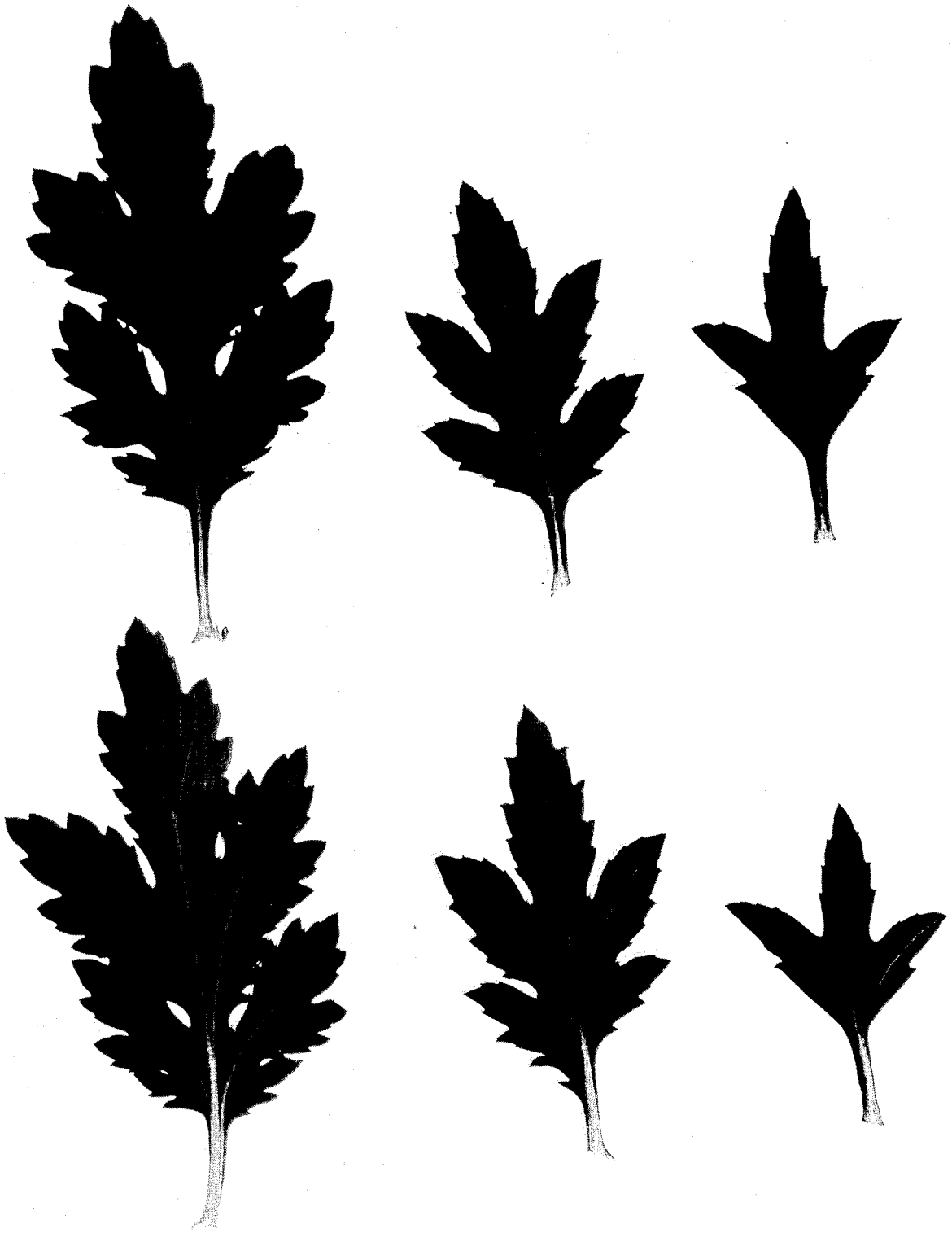

UNITED STATES PATENT AND TRADEMARK OFFICE

CERTIFICATE OF CORRECTION

PATENT NO. : Plant 6,880

DATED : June 27, 1989

INVENTOR(S) : Cornelis P. VandenBerg

It is certified that error appears in the above—identified patent and that said Letters Patent is hereby corrected as shown below:

Column 1, line 16, "200 rads" should be changed to --2000 rads--.

Column 1, line 20, "vegatative" should be changed to --vegetative--.

Signed and Sealed this

Twelfth Day of March, 1991

*Attest:*

HARRY F. MANBECK, JR.

*Attesting Officer*

*Commissioner of Patents and Trademarks*